United States Patent
Mujawar et al.

(10) Patent No.: US 9,995,724 B2
(45) Date of Patent: Jun. 12, 2018

(54) MERCURY DETECTING PAPER AND METHOD OF USING THE SAME

(71) Applicant: KING ABDULAZIZ UNIVERSITY, Jeddah (SA)

(72) Inventors: Liyakat Hamid Mujawar, Jeddah (SA); Iqbal M. I. Ismail, Jeddah (SA); Mohammad Soror El-Shahawi, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 206 days.

(21) Appl. No.: 15/163,604

(22) Filed: May 24, 2016

(65) Prior Publication Data
US 2017/0343524 A1 Nov. 30, 2017

(51) Int. Cl.
*G01N 33/18* (2006.01)
*G01N 31/22* (2006.01)

(52) U.S. Cl.
CPC ......... *G01N 33/1813* (2013.01); *G01N 31/22* (2013.01)

(58) Field of Classification Search
CPC ........................... G01N 33/1813; G01N 31/22
See application file for complete search history.

(56) References Cited

U.S. PATENT DOCUMENTS 5,612,184 A 3/1997 Rosson

FOREIGN PATENT DOCUMENTS

| CN | 102207502 A | 10/2011 |
|---|---|---|
| CN | 102706873 A | 10/2012 |
| CN | 103487431 A | 1/2014 |
| CN | 203643341 U | 6/2014 |
| KR | 2015-0046616 A | 4/2015 |
| KR | 20150046616 | * 4/2015 |

OTHER PUBLICATIONS

Hexamethyldisilazane Modified Paper as an Ultra-sensitive Platform for Visual Detection of Hg2+, Co2+, Zn2+ and the Application to Semi-quantittive Determination of Hg2+ in Wastewater Liyakat Hamid Mujawar, Adel Abdulazziz Felemban, and Mohammad Soror El-Shahawi Analyticas Science May 2016, vol. 32.*

Hamza et al., "Part 1. Spectrophotometric determination of trace mercury (II) in dental-unit wastewater and fertilizer samples using the novel reagent 6-hydroxy-3-(2-oxoindolin-3-ylideneamino)-2-thioxo-2H-1,3-thiazin-4(3H)-one and the dual-wavelength β-correction spectrophotometry," Journal of Hazardous Materials, 178 (2010) 287-292.

* cited by examiner

*Primary Examiner* — Krishnan S Menon
*Assistant Examiner* — Dwan A Gerido
(74) *Attorney, Agent, or Firm* — Richard C. Litman

(57) ABSTRACT

The mercury detecting paper provides a visual indication of the presence of mercury in an applied water sample. The mercury detecting paper is formed as a hydrophobic substrate having a reagent layer deposited thereon. The hydrophobic substrate is made from paper having a layer of hexamethyldisilazane (HMDS) deposited thereon, and the reagent layer is a layer of 6-hydroxy-3-(2-oxoindolin-3-ylideneamino)-2-thioxo-2H-1,3-thiazin-4(3H)-one (HOTT). In use, a water sample is applied to the reagent layer and a visual color change of the reagent layer upon contact with the water sample indicates a presence of mercury in the water sample. Specifically, HOTT turns a brick red color upon contact with $Hg^{2+}$ ions.

3 Claims, 4 Drawing Sheets

MERCURY DETECTING PAPER AND METHOD OF USING THE SAME

BACKGROUND OF THE INVENTION

1. Field of the Invention

The present invention relates to detection of metal ions in water, and particularly to a paper-based detector for $Hg^{2+}$ ions in water.

2. Description of the Related Art

Mercury and most of its compounds are extremely toxic to humans. Due to a wide variety of industrial processes, environmental contamination with mercury and mercury compounds is a pressing concern. One common form of mercury contamination in the environment is via mercury-contaminated wastewater from a wide variety of industrial plants, which may then contaminate natural water sources and reservoirs for drinking water.

A wide variety of testing systems and techniques exist for heavy metals. Due to the common necessity of testing in the field, a relatively simple and easy to use assay kit for mercury and the like is desirable. Although testing kits using a wide variety of reagents, microfluidic sensors and the like exist, such kits are often difficult to manufacture, difficult to use, and/or expensive. Recent efforts have been made to develop rapid assays using low-cost cellulose based platforms, such as filter paper. Although, the high degree of capillary action of such a filter paper substrate makes them an excellent platform in rapid assays in analytical and bioanalytical applications, their specific usage for testing of wastewater and the like is limited, due to their inherently hydrophilic nature.

Thus, mercury detecting paper and a method of using the same solving the aforementioned problems is desired.

SUMMARY OF THE INVENTION

The mercury detecting paper provides a visual indication of the presence of mercury in an applied water sample. The mercury detecting paper is formed as a hydrophobic substrate having a reagent layer deposited thereon. The hydrophobic substrate is made from paper having a layer of hexamethyldisilazane (HMDS) deposited thereon, and the reagent layer is a layer of 6-hydroxy-3-(2-oxoindolin-3-ylideneamino)-2-thioxo-2H-1,3-thiazin-4(3H)-one (HOTT).

In use, a water sample is applied to the reagent layer and a visual color change of the reagent layer upon contact with the water sample indicates a presence of mercury in the water sample. Specifically, HOTT turns a brick red color upon contact with $Hg^{2+}$ ions.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The mercury detecting paper provides a visual indication of the presence of mercury in a water sample. The mercury detecting paper is formed as a hydrophobic substrate having a reagent layer deposited thereon. The hydrophobic substrate is made from paper having a layer of hexamethyldisilazane (HMDS) deposited thereon, and the reagent layer is a layer of 6-hydroxy-3-(2-oxoindolin-3-ylideneamino)-2-thioxo-2H-1,3-thiazin-4(3H)-one (HOTT). Preferably, the paper is filter paper, such as, for example, Whatman® qualitative filter paper, Grade 4, manufactured by Whatman® Paper Ltd. of the United Kingdom. The HMDS layer may be deposited on the paper by any suitable method, such as chemical vapor deposition, for example.

Figure 1:
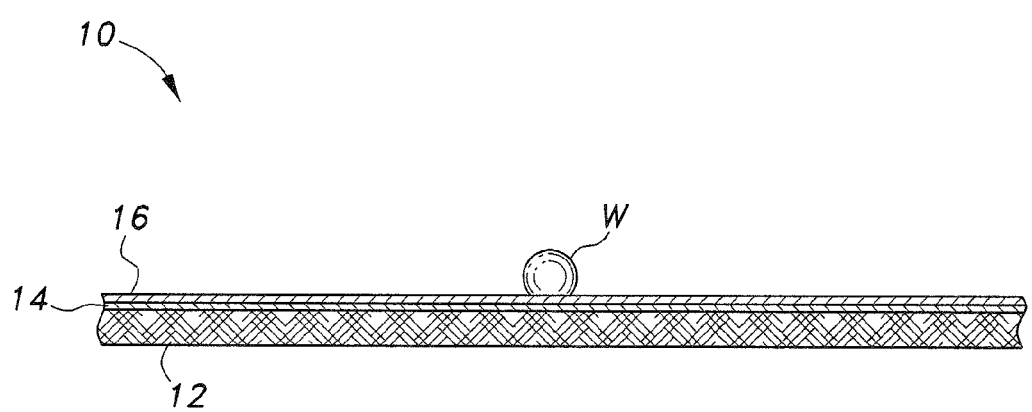
FIG. 1 is a partial side view in section of mercury detecting paper according to the present invention.

As illustrated in FIG. 1, chemical vapor deposition of the HMDS 14 on the highly hydrophilic paper 12 produces a low wetting (i.e., hydrophobic) substrate formed from a thin film of the HMDS 14 on the filter paper 12. The reagent layer 16 is formed on the hydrophobic substrate. Whereas untreated filter paper would result in a water contact angle of 0°, the mercury detecting paper 10, formed from the hydrophobic substrate, can have a contact angle with water sample W of approximately 128°.

In use, the water sample W is applied to the reagent layer 16 and a visual color change of the reagent layer 16 upon contact with the water sample W indicates a presence of mercury in the water sample W. Specifically, HOTT turns a brick red color upon contact with $Hg^{2+}$ ions. Due to the low wettability of the mercury detecting paper 10, a metal ion containing droplet localizes on the reagent spot and evaporates in a confined area. The colored complex formed from the accumulation of metal ions on the ligand spot results in enhancement of signal density per spot, which in turn enhances the limit of detection (LOD). The full development of the colored indicator spots on mercury detecting paper 10 takes between 5 and 10 minutes.

In comparison with pristine filter paper (i.e., filter paper which is not treated with the hydrophobic HMDS layer), the mercury detecting paper 10 has an assay sensitivity which is greater by five orders of magnitude, providing visual detection of the presence of mercury ions in the sub-ppm range (i.e., 0.5 ppb). It should be noted that the observed LOD of mercury detecting paper 10 is also lower than the maximum allowable level (MAL) of the tested metal ions by the World Health Organization (WHO) in water.

Figure 2A:
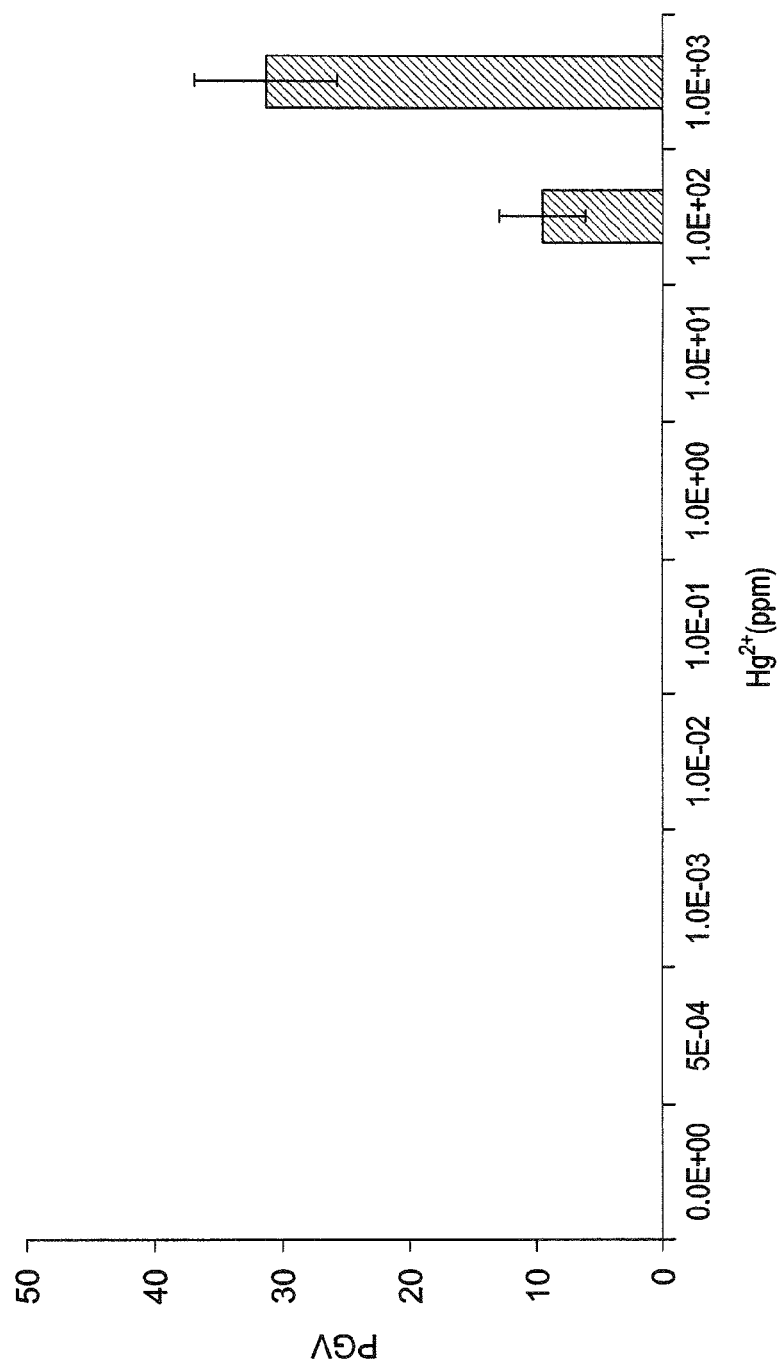
FIG. 2A is a graph showing detected pixel gray volume (PGV) as a function of mercury concentration of a water sample as detected by a conventional paper-based detector.
Figure 2B:
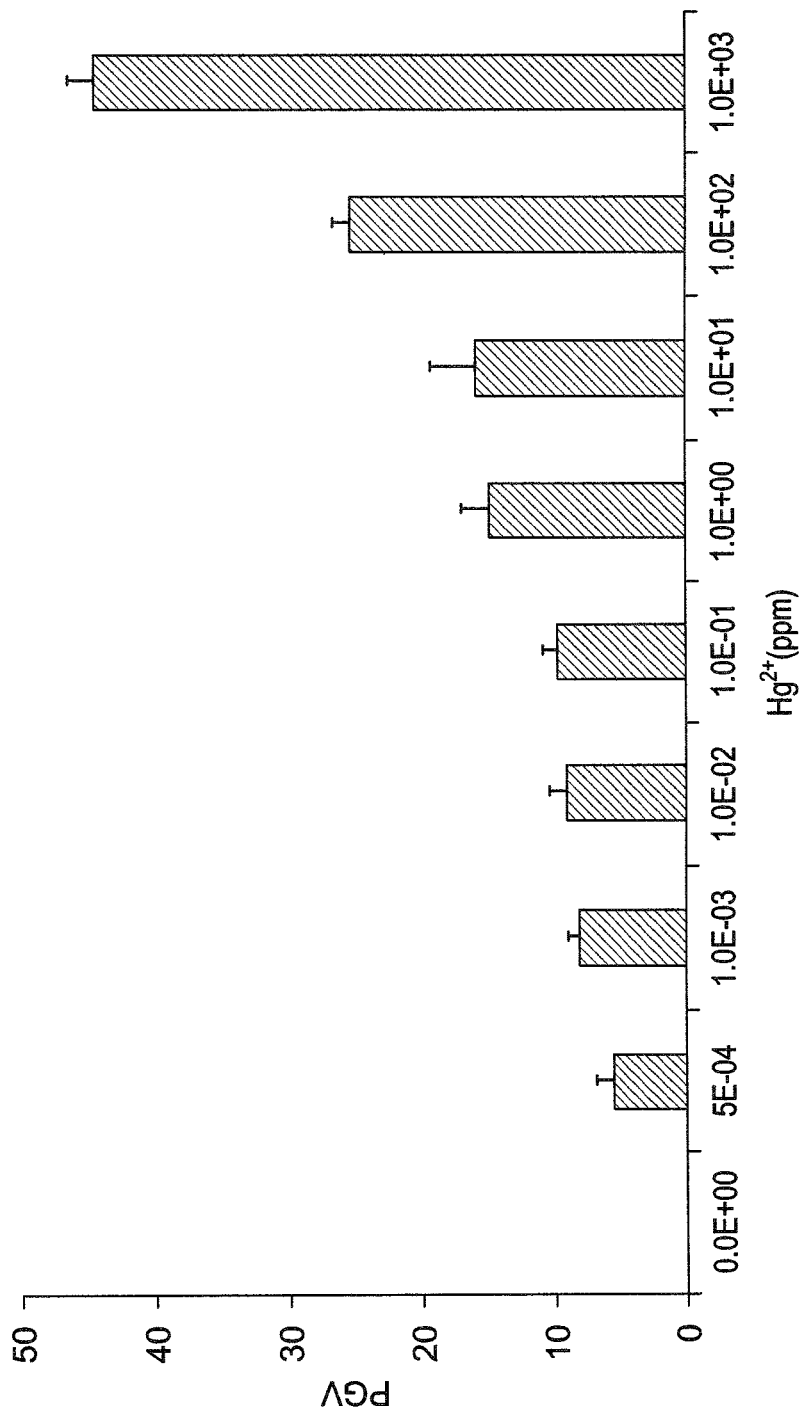
FIG. 2B is a graph showing detected pixel gray volume (PGV) as a function of mercury concentration of a water sample as detected by the mercury detecting paper according to the present invention.

As noted above, the mercury detecting paper 10 was tested against a pristine, or control paper sample, i.e., filter paper with a HOTT reagent, but without the additional hydrophobic HMDS layer. FIG. 2A is a graph showing detected pixel gray volume (PGV) as a function of mercury concentration as detected by the pristine, or control paper sample with a HOTT reagent, but without the additional hydrophobic HMDS layer. FIG. 2B is a graph showing PGV as a function of mercury concentration as detected by the present mercury detecting paper 10. Each set of PGV values were calculated using the National Institutes of Health's ImageJ image processing program. As shown in FIG. 2A, the pristine paper detector only indicates color change for a $10^2$ and $10^3$ ppm $Hg^{2+}$ ion solution, e.g., only for $Hg^{2+}$ concentrations of $10^2$ ppm or greater, hence no PGV was calculated for concentrations below $10^2$ ppm. However, on mercury detecting paper 10, the initially yellow colored HOTT spots were transformed into brick-red colored spots at even extremely low $Hg^{2+}$ concentrations (i.e., $5\times10^{-4}$ ppm).

The color intensity of the $Hg^{2+}$ spots can be easily read via the naked eye, with increasing intensity as a function of increasing concentration of $Hg^{2+}$, as can be seen in FIG. 2B. The HOTT reagent has numerous coordination sites in complex formations, which give variable bonding modes with the metal ions. A comparison of the IR spectra of the HOTT and its Hg(II) complex has revealed that the reagent participates with Hg(II) in a bi-dentate mono negative fashion through thione sulfur v(—N—C=S), as indicated from an observed shift of v(—N—C=S) to a lower wave number with the appearance of a new band at 395 $cm^{-1}$ due to v(Hg—S). Participation of the oxime oxygen of the reagent was also noticed from the disappearance of v-OH and the appearance of v(—Hg—O) at 1100 $cm^{-1}$ and v(Hg—O) at 549 $cm^{-1}$. Thus, it can be concluded that the HOTT reagent coordinates to Hg(II) via hydroxyl oxygen of the oxime and sulfur of thione foaming a six-membered ring chelate in a 1:2 Hg:HOTT molar ratio; i.e., $Hg(HOTT)_2$.

The performance and reproducibility of the one-step assay on both the pristine paper and mercury detecting paper 10 were performed by recording the data of three sets of experiments on both substrates. On the pristine paper, the spots of the HOTT reagent developed color only for $10^2$ and $10^3$ ppm concentration of $Hg^{2+}$, thus no PGV was calculated for $Hg^{2+}$ concentrations below $10^2$ ppm. As the ImageJ image analysis software is equipped to capture the presence of any available pixels, failure to calculate any PGV of assay spots on the pristine paper indicates very limited usage for rapid detection of $Hg^{2+}$. On mercury detecting paper 10, however, the PGV increased proportionally from $5\times10^{-4}$ ppm (i.e., 0.5 ppb) to $10^3$ ppm, as shown in FIG. 2B; i.e., quantitative data for all $Hg^{2+}$ concentrations is available.

On the pristine paper, the metal ion droplet spreads immediately in the X—Y (i.e., horizontal) as well as in the Z (i.e., vertical) direction, thus causing the analyte molecules to be dispersed throughout the ligand spot area. During this process, the colored (ligand-analyte) complex also diffuses, thereby reducing the density of the colored complex formation. At high analyte concentrations, the dispersion of analyte molecules has the least effect on color formation, but at low concentrations, no visible color develops. However, due to the hydrophobic nature of mercury detecting paper 10, the spreading of the aqueous droplet is restricted in the X—Y direction alone, thus the diffusion of the analyte molecules is confined to a limited region. The increased density of the analyte molecules reacts with the ligand molecules which, in turn, enhance the signal density. This phenomenon may be less effective at high analyte concentrations where the signal density is already strong, whereas at low concentrations, the amassing of analyte molecules in the limited spot area may enhance the signal density. Thus, on the mercury detecting paper 10, the development of the visible colored complex is more prominent even at low analyte concentrations, when compared against the pristine filter paper sample.

Figure 3:
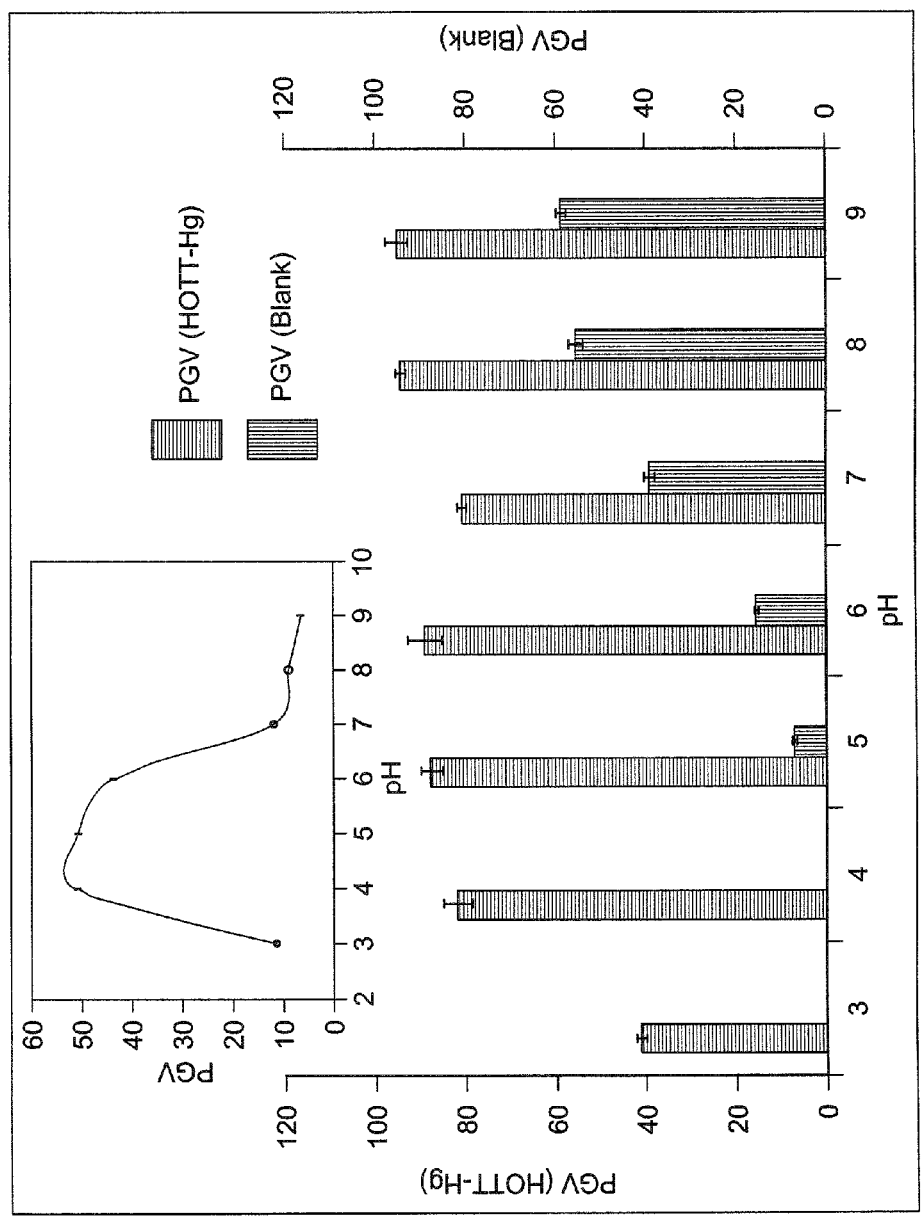
FIG. 3 is a graph showing detected pixel gray volume (PGV) as a function of pH of a water sample as detected by the mercury detecting paper, both for an active reagent spot and for a blank spot on the mercury detecting paper.

The influence of pH on the color intensity of the developed colored Hg-HOTT complex was investigated using a Britton-Robinson buffer (pH 3-9) and $Hg^{2+0}$ (100 ppm) solution. As shown in FIG. 3, the PGV values for the HOTT-Hg complex ($PGV_{Complex}$) increased gradually up to pH 4-6, while at the same time, the PGV of a blank spot (i.e., a negative control) was also increased. The dissociation of the oxime hydroxyl group at this pH 4-6 may account for the observed change. At solution pH 7-9, the $PGV_{Blank}$ value negatively affected the signal-to-noise ratio of the one-step assay. This behavior is most likely attributed to the hydrolysis of the $Hg(HOTT)_2$ complex at pH>7. The normalized PGV ($PGV_{Complex}-PGV_{Blank}$) value with respect to pH is in the form of a bell-shaped curve, as shown in the inset of FIG. 3, which clearly indicates the optimum pH range of 4-6.

It is to be understood that the present invention is not limited to the embodiments described above, but encompasses any and all embodiments within the scope of the following claims.

We claim:
1. A mercury detecting paper, comprising:
   a hydrophobic substrate, the hydrophobic substrate including paper having a layer of hexamethyldisilazane deposited thereon; and
   a reagent layer formed on the hydrophobic substrate, the reagent layer comprising 6-hydroxy-3-(2-oxoindolin-3-ylideneamino)-2-thioxo-2H-1,3-thiazin-4(3H)-one,
   whereby a visual color change of said reagent layer upon contact with a water sample indicates a presence of $Hg^{2+}$ ions in the water sample.
2. The mercury detecting paper as recited in claim 1, wherein the paper comprises filter paper.
3. A method of detecting mercury, comprising the steps of:
   providing mercury detecting paper, the mercury detecting paper including a reagent layer formed on a hydrophobic substrate, the hydrophobic substrate including paper having a layer of hexamethyldisilazane deposited thereon, and the reagent layer comprising 6-hydroxy-3-(2-oxoindolin-3-ylideneamino)-2-thioxo-2H-1,3-thiazin-4(3H)-one;
   applying a water sample to the reagent layer of the mercury detecting paper; and
   visually observing the reagent layer, wherein a visual color change of the reagent layer indicates a presence of $Hg^{2+}$ ions in the water sample.

\* \* \* \* \*